(12) United States Patent
Mundwiler et al.

(10) Patent No.: US 7,665,990 B2
(45) Date of Patent: *Feb. 23, 2010

(54) DENTAL IMPLANT WITH POSITIONING MEANS

(75) Inventors: Ulrich Mundwiler, Tenniken (CH); Marcello Memmolo, Sissach (CH)

(73) Assignee: Straumann Holding AG (CH)

( * ) Notice: Subject to any disclaimer, the term of this patent is extended or adjusted under 35 U.S.C. 154(b) by 254 days.

This patent is subject to a terminal disclaimer.

(21) Appl. No.: 10/594,109

(22) PCT Filed: Mar. 24, 2005

(86) PCT No.: PCT/EP2005/003140
§ 371 (c)(1),
(2), (4) Date: Sep. 25, 2006

(87) PCT Pub. No.: WO2005/092235
PCT Pub. Date: Oct. 6, 2005

(65) Prior Publication Data
US 2007/0196786 A1 Aug. 23, 2007

(30) Foreign Application Priority Data
Mar. 25, 2004 (EP) .................. 04007244

(51) Int. Cl.
*A61C 8/00* (2006.01)
(52) U.S. Cl. ...................... 433/173; 433/174
(58) Field of Classification Search ................ 433/173, 433/174, 175, 201.1
See application file for complete search history.

(56) References Cited

U.S. PATENT DOCUMENTS

| 4,960,381 | A | | 10/1990 | Niznick | |
|---|---|---|---|---|---|
| 5,116,225 | A | * | 5/1992 | Riera | 433/173 |
| 5,246,370 | A | * | 9/1993 | Coatoam | 433/173 |
| 5,302,126 | A | * | 4/1994 | Wimmer et al. | 433/173 |
| 5,782,918 | A | * | 7/1998 | Klardie et al. | 606/60 |
| 5,810,592 | A | * | 9/1998 | Daftary | 433/173 |
| 5,823,776 | A | * | 10/1998 | Duerr et al. | 433/173 |
| 5,890,902 | A | * | 4/1999 | Sapian | 433/173 |

(Continued)

FOREIGN PATENT DOCUMENTS

DE 100 48 564 A 1 3/2002

(Continued)

*Primary Examiner*—Cris L Rodriguez
*Assistant Examiner*—Hao D Mai
(74) *Attorney, Agent, or Firm*—Scully, Scott, Murphy & Presser, P.C.

(57) ABSTRACT

The present invention relates to an intraosteal dental implant (1) including a bore (14) in the form a blind hole, the bore (14) being shaped and devised such as to rotationally secure an abutment (6) receivable in the dental implant (1), wherein the bore (14) is provided with a substantially cylindrical sleeve (15) extending coaxially to the dental implant (1), wherein the dental implant (1) includes an inner neck surface (18), and wherein an intersection curve (20) between the inner neck surface (18) of the dental implant (1) and the sleeve (15) does not lay in a plane perpendicular to the axis (7) of the dental implant (1) or wherein the inner neck surface (18) of the dental implant (1) has a substantially conical shape with an imaginary tip (19) offset from the axis (7) of the dental implant (1).

30 Claims, 8 Drawing Sheets

U.S. PATENT DOCUMENTS

| | | | |
|---|---|---|---|
| 6,102,702 A * | 8/2000 | Folsom et al. | 433/172 |
| 6,116,904 A * | 9/2000 | Kirsch et al. | 433/173 |
| 6,537,069 B1 * | 3/2003 | Simmons, Jr. | 433/173 |
| 6,537,070 B1 * | 3/2003 | Stucki-McCormick | 433/174 |
| 6,648,643 B2 * | 11/2003 | Hollander et al. | 433/173 |
| 6,663,388 B1 * | 12/2003 | Schar et al. | 433/173 |
| 6,892,998 B2 * | 5/2005 | Newton | 251/149.1 |
| 6,939,135 B2 * | 9/2005 | Sapian | 433/174 |
| 7,014,464 B2 * | 3/2006 | Niznick | 433/173 |
| 7,056,117 B2 * | 6/2006 | Simmons, Jr. | 433/173 |
| 7,300,282 B2 * | 11/2007 | Sapian | 433/173 |
| 7,329,124 B2 * | 2/2008 | Mundwiler et al. | 433/173 |
| 2003/0104337 A1 * | 6/2003 | Cottrell | 433/173 |
| 2003/0224328 A1 * | 12/2003 | Sapian | 433/173 |

FOREIGN PATENT DOCUMENTS

| | | |
|---|---|---|
| EP | 0 868 889 A1 | 10/1998 |
| EP | 0 879 580 A2 | 11/1998 |
| EP | 1 205 158 A1 | 5/2002 |
| EP | 1 371 342 A1 | 12/2003 |

* cited by examiner

DENTAL IMPLANT WITH POSITIONING MEANS

TECHNICAL FIELD

The present invention relates in general to an improved intraosteal dental implant with positioning means for an abutment or the like.

BACKGROUND OF THE INVENTION

Intraosteal implants are widely used in dental restorations to support fixed or removable prostheses where the natural root of a teeth has been lost.

One problem incurred by the implants is the correct positioning of an abutment or the like within the dental implant and to rotationally lock the abutment or the like thereon.

To alleviate the above problems various solutions have been proposed by the prior art including the solution of U.S. Pat. No. 4,960,381 wherein the implant is provided with a blind bore including a hexagonal shaped section exactly matching a complementary section on the abutment. Accordingly, the abutment can clamped in a rotationally stationary manner to the dental implant by means of a fixing screw extending through and engaging the abutment. In addition, the fixing screw threadingly engages the dental implant.

Furthermore, from EP-A-1 371 342 or EP-A-868 889 there is known a dental implant with slanted plane surfaces cooperating with complementary matching plane surfaces on an abutment or the like in order to keep the latter in an angularly fixed position. A dental implant with an oval blind bore is known from EP-A-1 205 158.

The above described known prior art dental implants, however, are not difficult to manufacture or do not provide for sufficient rotational stability of the abutment or a superimposed secondary part.

SUMMARY OF THE INVENTION

In view of the above it is an object of the invention to provide for an improved intraosteal dental implant which avoids the drawbacks of the prior art and which includes simple and reliable positioning means for an abutment or the like.

Another object of the present invention is to provide an abutment or the like suitable for the dental implant of the present invention.

The foregoing objects as well as further objects which will become apparent hereinafter are achieved by the novel intraosteal dental implant as defined in the appended claims.

BRIEF DESCRIPTION OF THE DRAWINGS

The foregoing and other objects, features, and advantages of the invention, as well as presently preferred embodiments thereof, will become more apparent from a reading of the following description, in connection with the accompanying drawings in which.

DESCRIPTION OF THE PREFERRED EMBODIMENTS

As used in the following description and claims the terms lower/upper, left/right and vertical/horizontal are only intended for illustrative purposes and are by no means conceived to limit the scope of the invention.

With reference to FIGS. 1A through 4, there is provided an intraosteal dental implant generally designated with reference numeral 1 with an apical tip 1'. The dental implant 1 has a bone tissue apposition surface 2 which is typically threaded and/or roughened in a known manner and extends into the alveolar bone in the inserted state of the dental implant. Although the shown dental implant has a screw like appearance, it will be appreciated by the person skilled in the art that other shapes like a root-like shape can be used without departing from the scope and spirit of the invention.

The coronal end of the bone apposition surface 2 defines a lower neck portion surface 2a. In addition the dental implant 1 is provided with a soft tissue apposition surface 3 extending from an upper end of the bone tissue apposition surface 2, at the neck portion surface 2a, up to a shoulder 5 of the dental implant 1. Thus, an interface 4 is defined between the bone tissue and soft tissue apposition surfaces. The soft tissue apposition surface 3 defines an upper neck portion of the dental implant 1. The upper neck portion surface 3 and the lower neck portion surface 2a define the neck of the dental implant 1.

As known in the art, the bone tissue apposition surface 2 may be provided with an additive or non-additive surface structure extending up to the interface 4 in order to enhance the osteal integration. Such structure surface is well known to the person skilled in the art of dental implantology and will not be further described (see for instance Ralf-J Kohal et al., "Wurzelanaloge Titaniunimplantate (Bio-Design-Implantate" für die Sofortimplantation—Das Re-Implant®-System", Implantologie 1996; 2: 99-115).

The soft tissue apposition surface or upper neck portion surface 3 is machined, for instance by polishing, to obtain a surface enhancing the regeneration and the attachment of the soft tissue. Again, the machining of the soft tissue apposition surface is known in the art (see for instance Ralf-J Kohal et al., "Wurzelanaloge Titaniumimplantate (Bio-Design-Implantate" für die Sofortimplantation—Das Re-Implant®-System", Implantologie 1996; 2: 99-115), and therefore the discussion thereof will be omitted in the present specification. Also the provision of additives for the soft tissue apposition surface, which is per se known in the alt, is envisaged by the present invention. Furthermore, other machining techniques, in addition to polishing, are envisaged and applicable to the present soft tissue apposition surface.

The plane of the shoulder 5 is inclined with respect to the axis 7 of the implant 1.

Figures 1A, 1B:
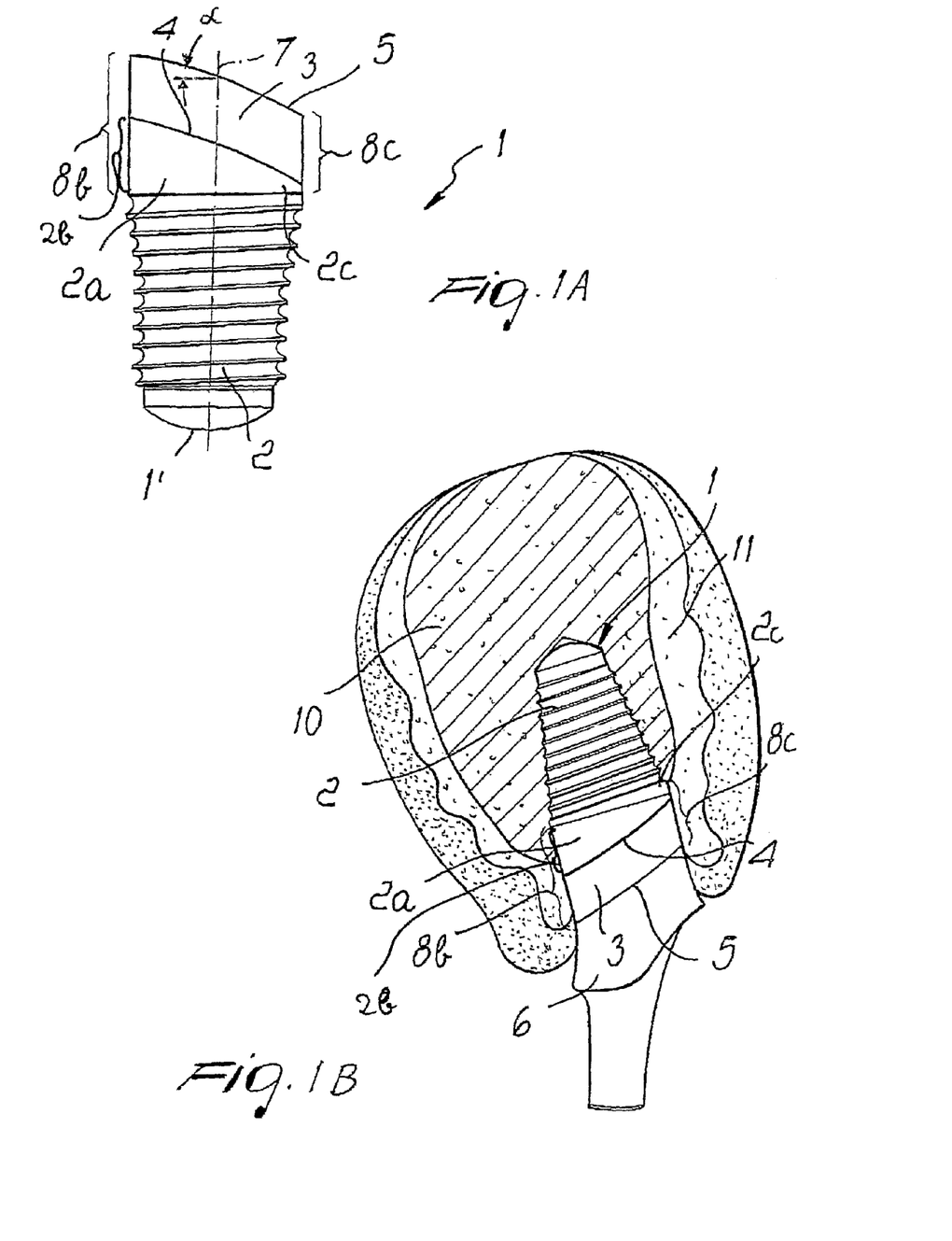
FIG. 1A is an interdental view of an intraosteal dental implant which can be provided with positioning means according to the present invention.
FIG. 1B is an interdental view of an intraosteal dental implant of FIG. 1A in the implanted state thereof.
Figure 2B:
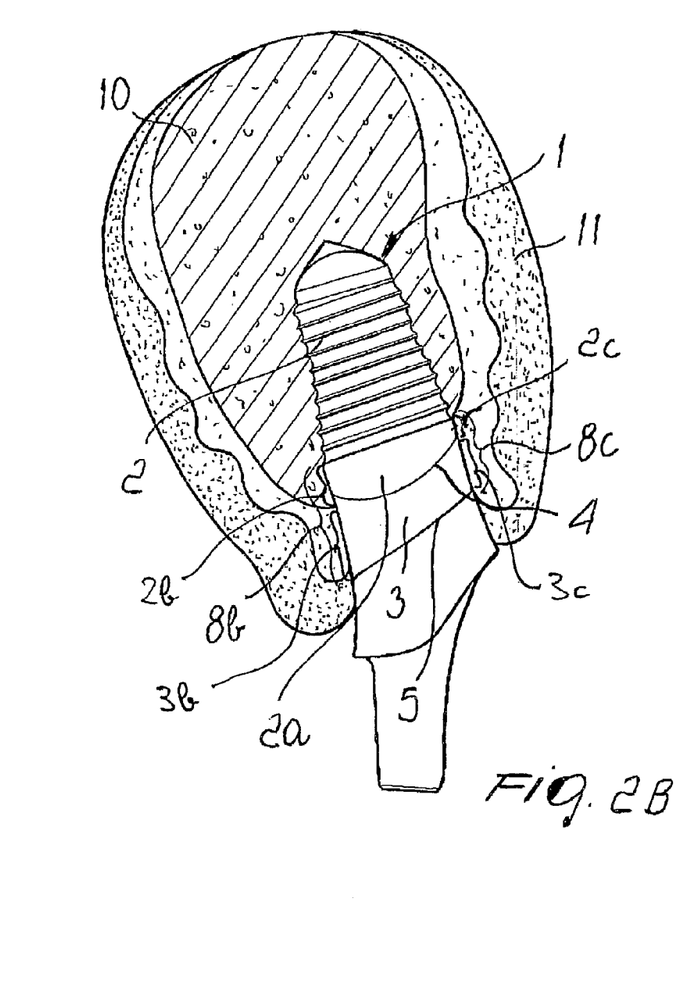
FIG. 2B is an interdental view of an intraosteal dental implant of FIG. 2A in the implanted state thereof.

The inclination reflects the morphologic difference between the palatal or lingual sides on one hand and the labial side on the other hand with respect to the alveolar bone anatomy. In other words, as shown in FIGS. 1B, 2B and 3B, in that particular case, the palatal side 8b of the dental implant 1 has a larger extension than the labial side 8c thereof. Similar considerations apply for a lower jaw bone implant where the lingual side of the dental implant has a larger extension than that of the labial side thereof.

The inclined shoulder 5 assures a neck palatal side 8b or a neck lingual side (not shown) which is higher than the neck labial side 8c. In view of the processing of the shoulder 5 the by means of milling, grinding or drilling with a conical tool the plane of the shoulder 5 may have a slightly curved shape. This is in particular the case if the dental implant 1 is devised with an inner neck surface 18 as shown and explained in conjunction with FIG. 5A.

The inclination of the plane of the shoulder 5 is preferably in the range from about 10° to about 30° with respect to the plane perpendicular to the axis 7 of the implant 1, as indicated with α in FIG. 1A. In other words the inclination with respect to the axis 7 is in the range from about 60° to about 80°.

More preferred is the range from about 15° to about 25° with respect to the plane perpendicular to the axis 7 of the implant 1. In other words the more preferred inclination with respect to the axis 7 is in the range from about 65° to about 75°.

The most preferred inclination of the plane of the shoulder 5 is of about 20° with respect to the plane perpendicular to the axis 7 of the implant 1 or about 70° with respect to the axis 7.

Figures 1C, 2A:
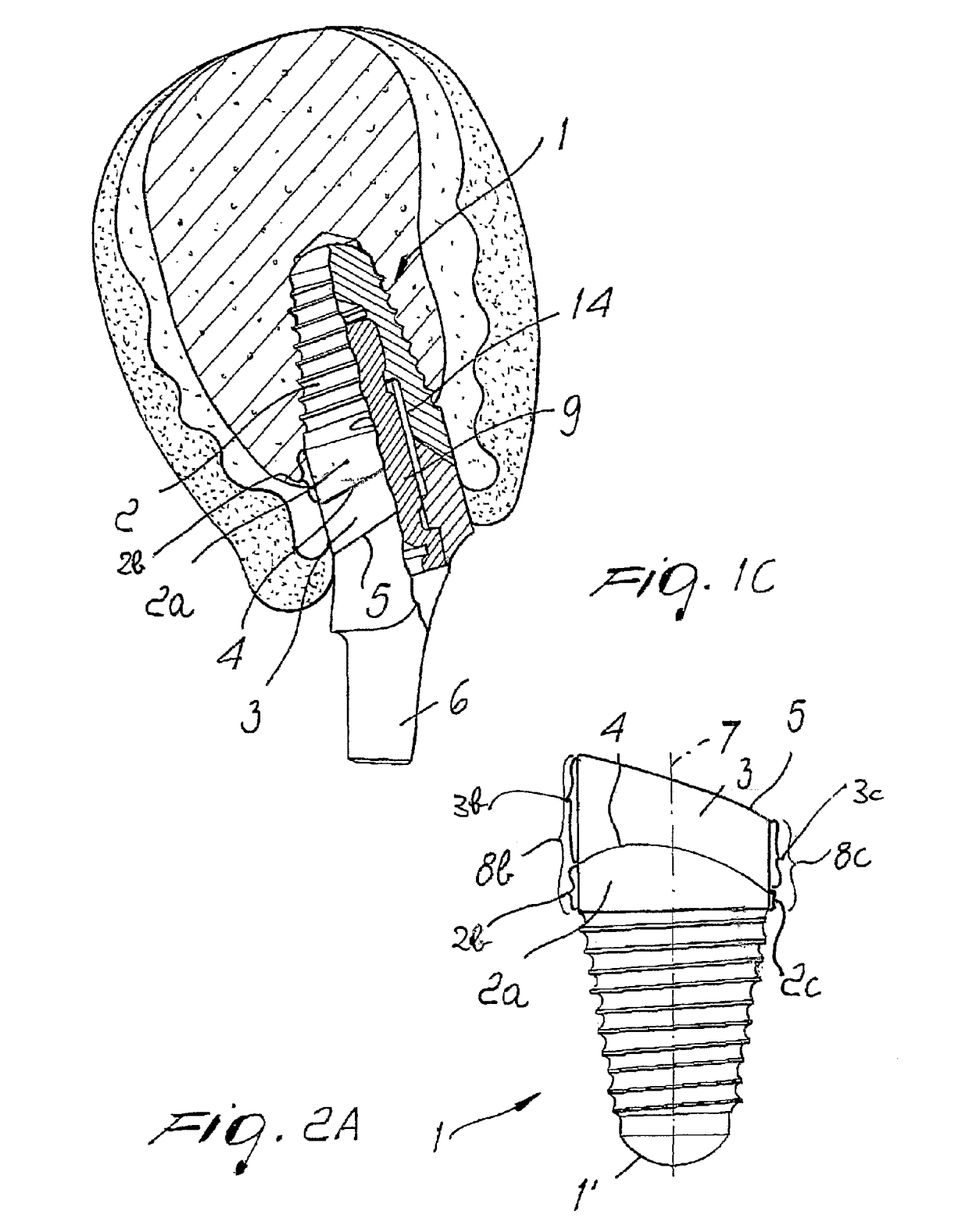
FIG. 1C is a partially cut away interdental view of an intraosteal dental implant of FIG. 1A in the implanted state thereof.
FIG. 2A is an interdental view of an intraosteal dental implant which can be provided with positioning means according to the present invention.

FIGS. 1A through 1C show the implant wherein the interface 4 between the lower neck portion surface 2a and the soft tissue apposition surface 3 lays in a plane and extends substantially in a parallel manner to the shoulder 5 of the dental implant 1 which also lays in a plane. In other words, the plane passing through the interface 4 is parallel to the plane passing through the shoulder 5. Accordingly, the lower neck portion surface 2a has a palatal side 2b which has a larger extension than a labial side 2c thereof. Same applies for the ratio between the lingual side of the lower neck portion and the labial side thereof. It is believed that the embodiment of the dental implant according to the first embodiment FIGS. 1A through 1C is particularly suitable for adjacent dental implants.

Preferably, the extension (width) of the soft tissue apposition surface 3 as defined by parallel interface 4 and shoulder 5 is in the range of about 0.5 to about 3 mm, and more preferred of about 1.8 mm.

FIG. 1B is an interdental view of an intraosteal dental implant 1 in the implanted state thereof. The dental implant 1 is located in the alveolar bone 10 which is schematically shown for explanatory purposes. The alveolar bone 10 is in contact with the soft tissue 11. According to FIG. 1B an abutment 6 can be apposed on the shoulder 5 of the dental implant 1. The abutment 6 is built to perfectly fit on the upper surface of shoulder 5 and to take into account the inclined shoulder 5 of the dental implant 1.

FIG. 1C further shows a section view of the dental implant 1. The section view shows a screw 9 located in a receiving bore 14 of the dental implant 1 which firmly fixes the abutment 6 to the dental implant 1. Furthermore, as described hereinafter, the abutment 6 may be advantageously provided in accordance with the invention with a downwardly extending protrusion fitting into a respective receiving bore of the implant 1 such as to rotationally secure the latter element to another.

It has been noted that the dental implant according to the above first embodiment provides for particular advantages if implemented as a two stage implant.

Figure 2C:
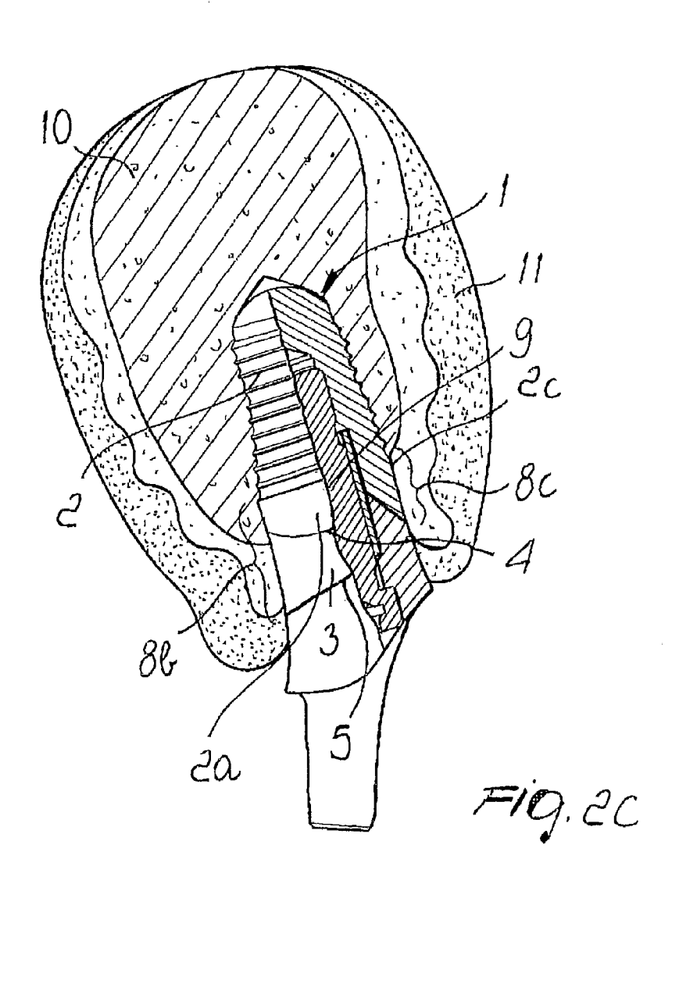
FIG. 2C is a partially cut away interdental view of an intraosteal dental implant according to FIG. 2A in the implanted state thereof.

According to a second embodiment, as shown in FIG. 2A through FIG. 2C, the interface 4 between the apposition surface 2a and the soft tissue apposition surface 3 has a curved profile similar to the interface (boundary) shown in WO-A-01 49 199. In particular, the curved profile of the interface 4 is such that it is increasing from the labial side towards the interdental side and decreasing towards the palatal/lingual side. The curved profile is designed to better reflect the bone-soft tissue profile around the cavity wherein the implant is intended to be located.

Preferably the extension (width) of the soft tissue apposition surface 3 as defined by the curved interface 4 is in the range of about 0.5 to about 3 mm, and more preferred of about 1.8 mm, at the labial side 3c, and in the range of about 0.5 to about 3 mm, and more preferred of about 2.8 nun, at the lingual/palatal side 3b.

Except for the curved profile of the interface 4 the second embodiment depicted in FIGS. 2A through 2C is the same as that of FIGS. 1A through 1C and therefore the same explanations as set forth in respect to the latter apply.

The inventors of the present invention surprisingly found that for predictable bone and soft tissue preservation the plane passing through the interface 4 must not be parallel to the plane passing through the shoulder 5. In particular, the second embodiment is believed to provide for a good bone tissue preservation notwithstanding the fact that the sloping of the interface 4 does not necessarily follow the outline of the bone tissue. Similar considerations apply to the third and fourth embodiments, respectively, which are described hereinbelow.

Figure 3A:
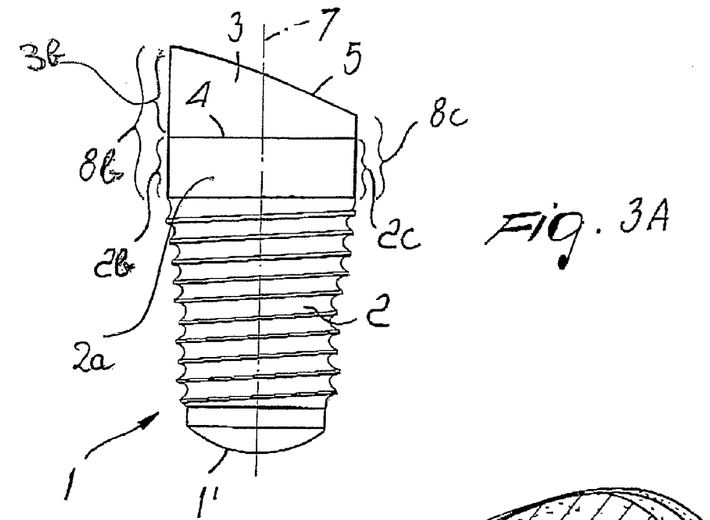
FIG. 3A is an interdental view of an intraosteal dental implant which can be provided with positioning means according to the present invention.
Figure 3B:
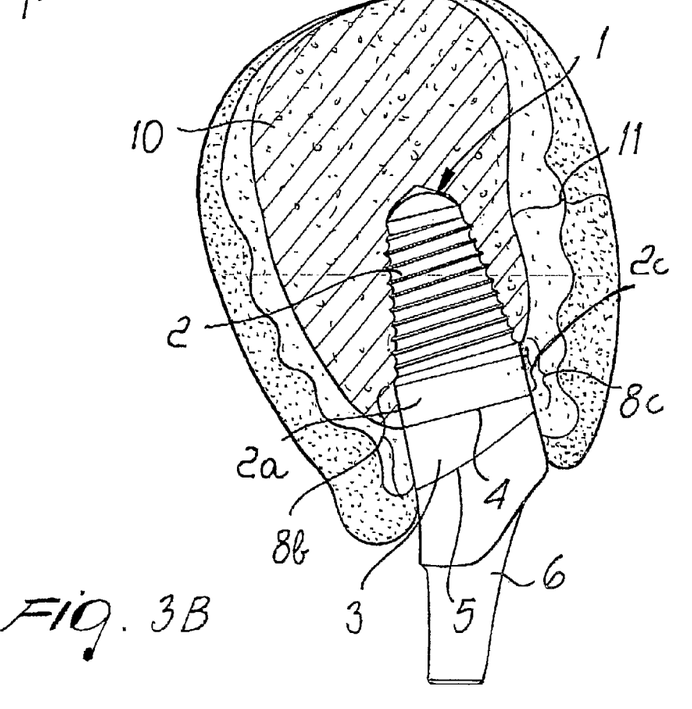
FIG. 3B is an interdental view of an intraosteal dental implant according to FIG. 3A in the implanted state thereof.
Figures 3C, 4:
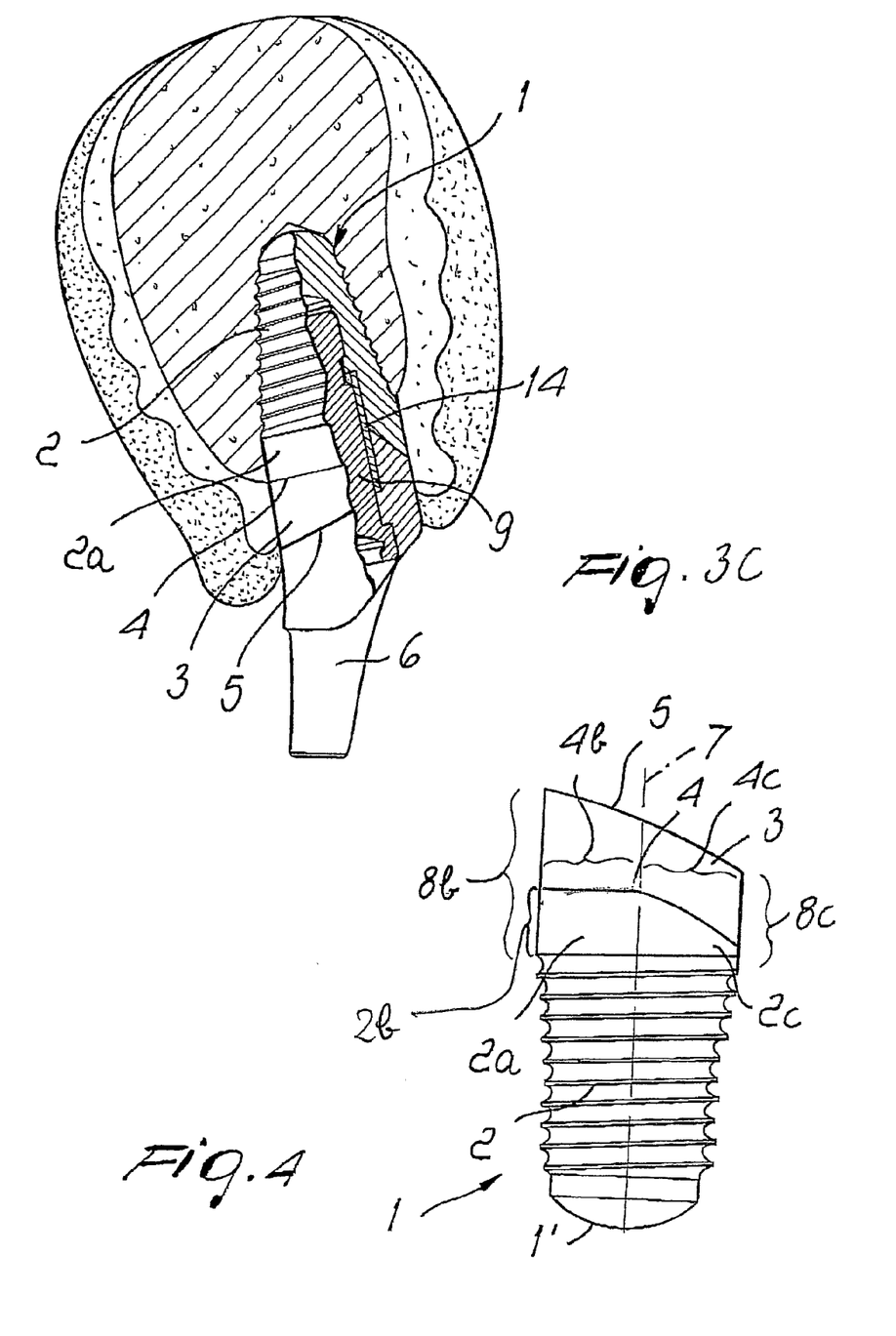
FIG. 3C is a partially cut away interdental view of an intraosteal dental implant according to FIG. 3A in the implanted state thereof.
FIG. 4 is an interdental view of an intraosteal dental implant which can be provided with positioning means according to the present invention.

According to a third embodiment, as shown in FIG. 3A through FIG. 3C, the interface 4 between the bone apposition surface 2 and the soft tissue apposition surface 3 lays in a plane substantially perpendicular to the axis 7 of the implant 1.

Preferably the extension (width) of the soft tissue apposition surface 3 as defined by the interface 4 perpendicular to the axis 7 of the dental implant 1 is in the range of about 0.5 to about 3 mm, and more preferred of about 2.3 mm at the palatal/lingual side 3b.

Except for the interface 4, which is substantially perpendicular to the axis 7 of the dental implant 1, the embodiment depicted in FIGS. 3A through 3C is the same as that of FIGS. 1A through 1C and therefore the same explanations as set forth in respect to the latter apply.

According to a fourth embodiment, as shown in FIG. 4, the palatal/lingual side 4b of the interface 4 between the bone tissue apposition surface 2 and the soft tissue apposition surface 3 lays in a plane which is substantially perpendicular to the axis 7 of the implant 1 and the labial side 4c of the interface 4 is curved. Basically, in the fourth embodiment the palatal/lingual side 4b of the interface 4 resembles to the corresponding side of the third embodiment while the curved labial side 4c of the interface 4 resembles to the corresponding side of the second embodiment.

Except for the interface 4, which is as described above, the embodiment depicted in FIG. 4 is the same as that of FIGS. 1A through 1C and therefore the same explanations as set forth in respect to the latter apply.

With reference to FIGS. 5A through 7 there is shown the preferred arrangement according to the present invention for the rotational positioning of the abutment 6 into the dental implant 1. The person skilled in the art will appreciate that the latter arrangement can be used with particular advantages in conjunction with the dental implants described above and also with further conventional prior art dental implants.

Figures 5A, 5B:
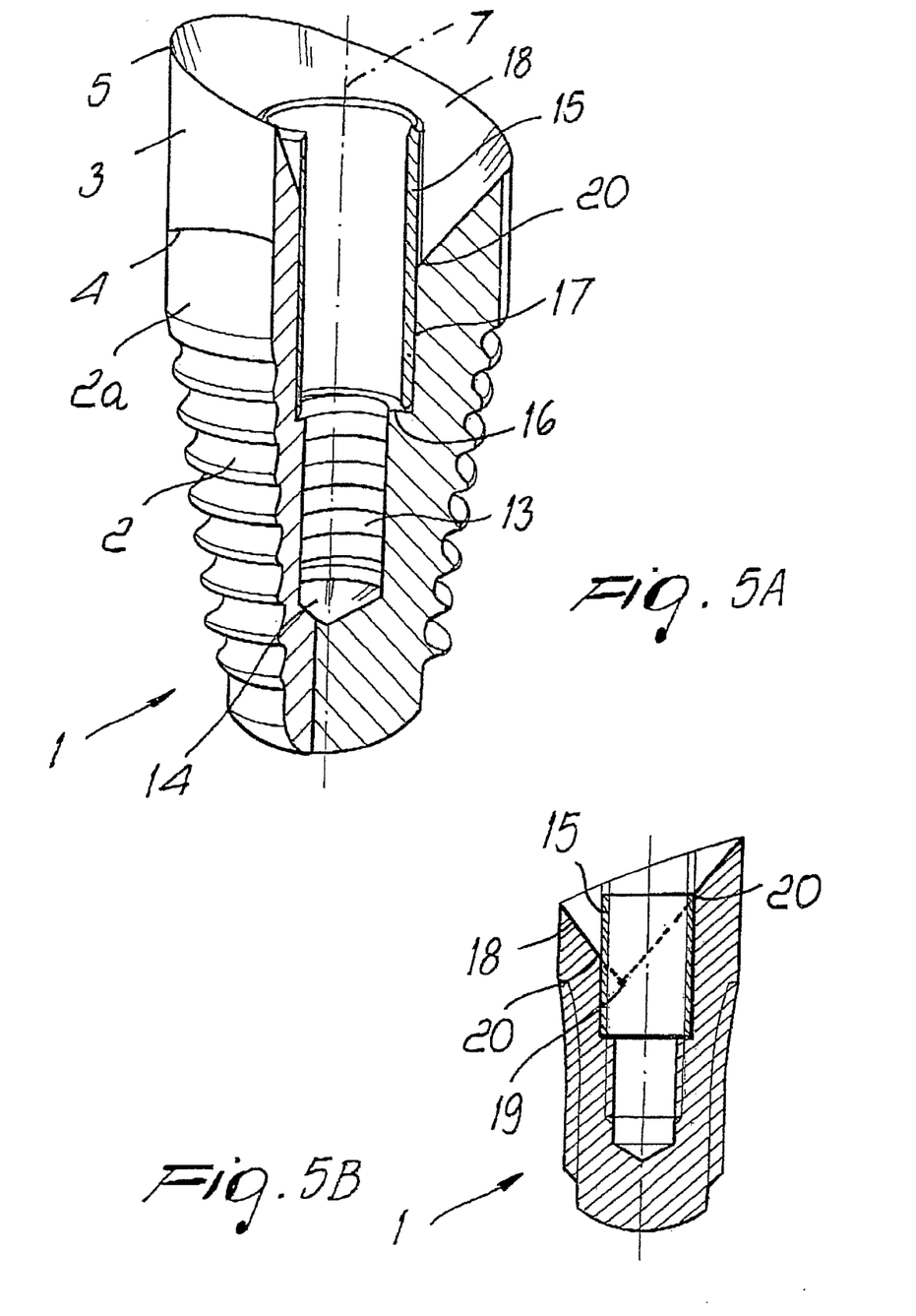
FIG. 5A shows the positioning means according to the present invention provided on varying dental implants along with varying abutments.
FIG. 5B shows the positioning means according to the present invention provided on varying dental implants along with varying abutments".

As shown in FIG. 5A the dental implant 1 is provided in a conventional manner with a receiving bore 14 in the form of a blind hole having an internal thread 13 and which extends axially from coronal to apical.

According to the invention, at the coronal end of the internal thread 13 of the receiving bore 14, there is provided a substantially circular rest surface 16 which extends in a perpendicular manner to the axis 7 of the implant and which receives substantially cylindrical sleeve 15. The sleeve 15 and the internal wall 17 of the bore 14 are sized such that the sleeve 15 precisely fits the internal wall 17. The sleeve 15 is fixedly retained in the space defined by the internal wall 17 and the rest surface 16.

Figure 6A:
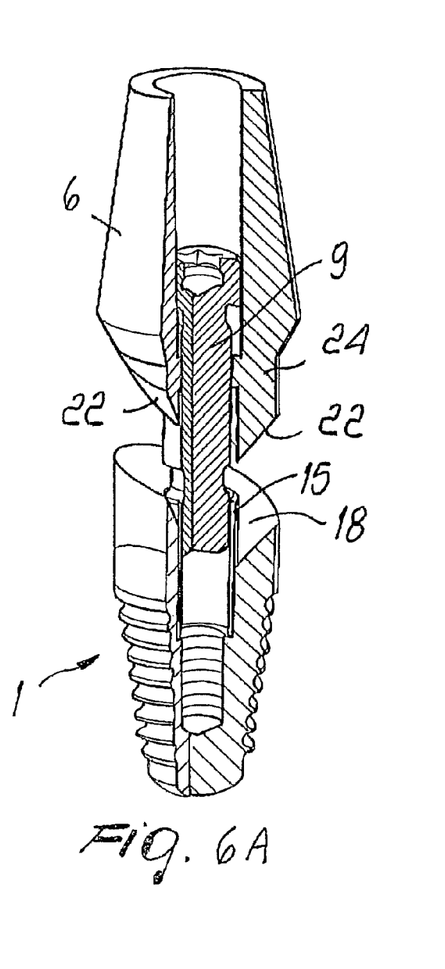
FIG. 6A shows the positioning means according to the present invention provided on varying dental implants along with varying abutments.
Figure 6B:
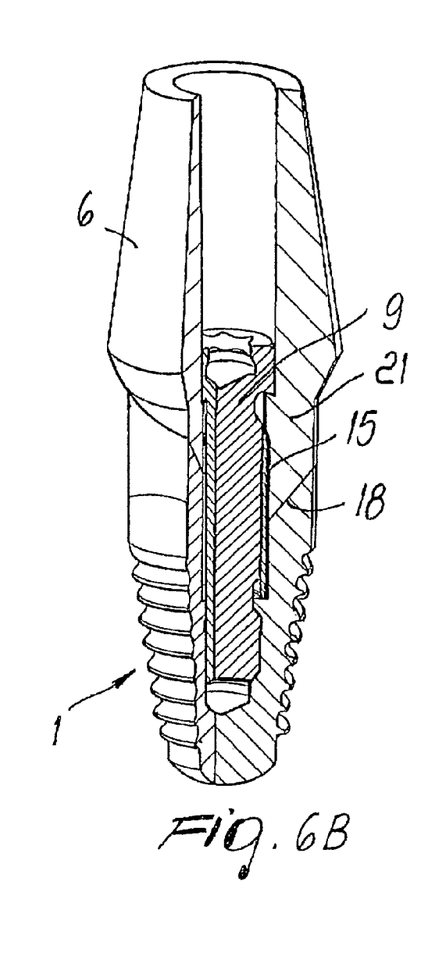
FIG. 6B shows the positioning means according to the present invention provided on varying dental implants along with varying abutments.
Figure 7:
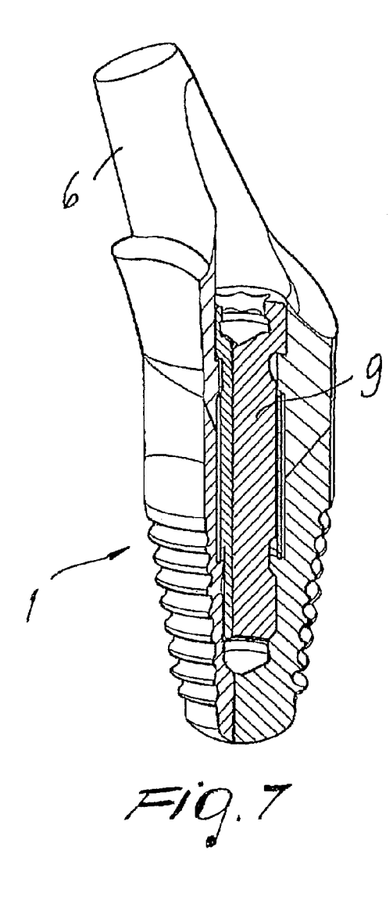
FIG. 7 shows the positioning means according to the present invention provided on varying dental implants along with varying abutments.

As shown in FIG. 5B, which is a sectional view of FIG. 5A, the inner neck surface 18 of the dental implant 1 defined below the shoulder 5 has, according to the invention, a substantially conical shape with an imaginary tip 19 offset from the axis 7 of the dental implant 1. In this way, a complementary shaped abutment 6, as shown in FIGS. 6A through 7, can be accommodated between the sleeve 15 and the inner neck surface 18 such that the abutment 6 is rotationally secured to the dental implant 1. It is noted that the rotational securing can also be achieved, according to the invention, by providing the intersection curve 20 between the inner neck surface 18 of the dental implant 1 and the sleeve 15 such that the intersection curve does not lay in or is inclined in respect to a plane perpendicular to the axis 7 of the dental implant 1.

FIGS. 6A and 6B show a straight abutment 6 having a downwardly extending protrusion 21 with a lower surface 22 exactly matching the inner neck surface 18 of the dental implant 1. As shown in FIG. 6B, in the assembled state of the abutment, the downwardly extending protrusion 21 surrounds the sleeve 15 and the lower surface 22 rests on the inner neck surface 18. The screw 9 also fits the sleeve 15 with no or very little play to improve the stability of the arrangement. The thread pitch of the screw is preferably from 0.5 to 1.3 mm and more preferred from 0.5 to 0.8 mm in order to improve the positioning of the abutment.

FIG. 7 shows an arrangement similar to that of FIGS. 6A and 6B, wherein the abutment is inclined.

Figure 8:
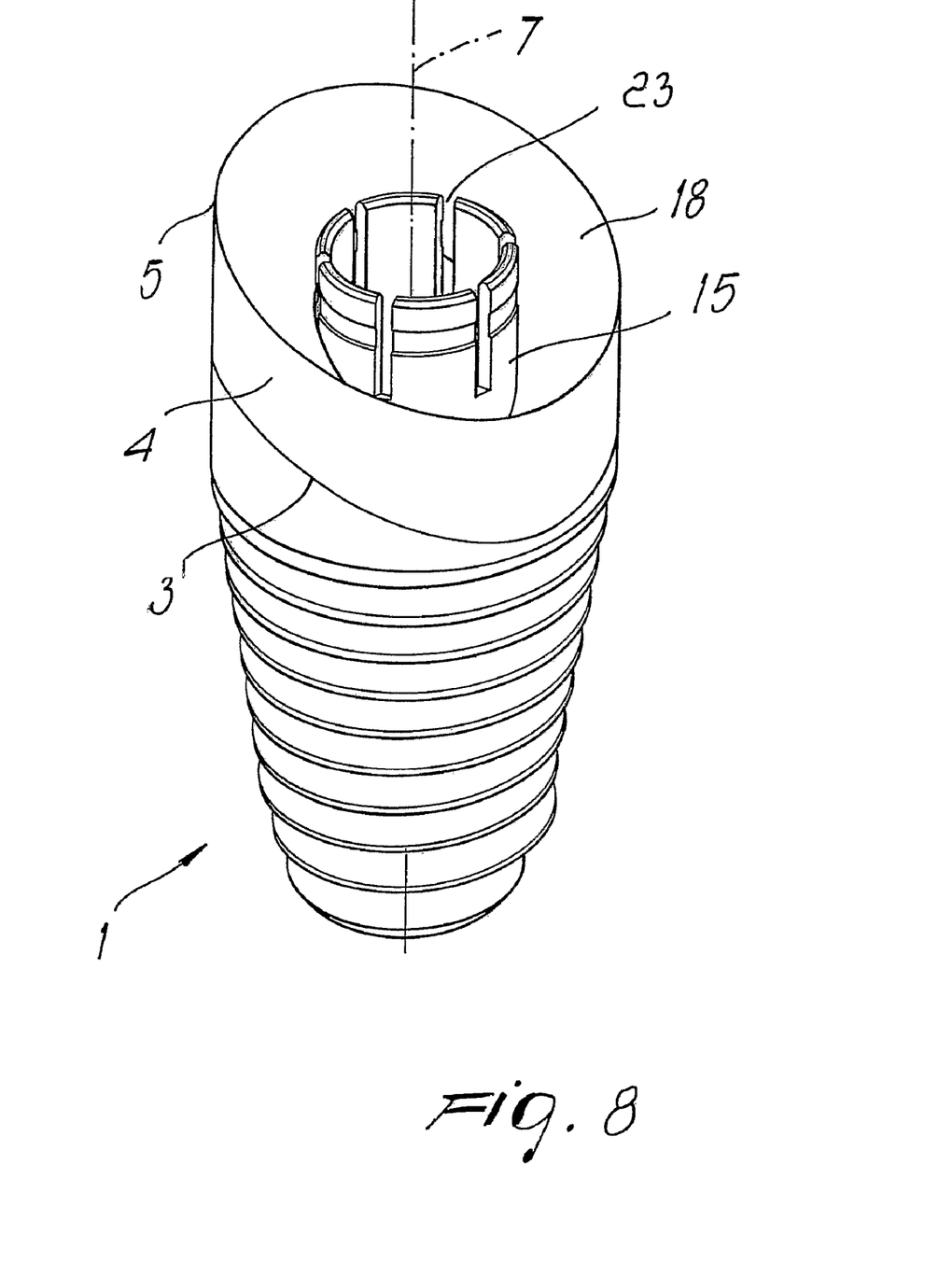
FIG. 8 shows the positioning means according to the present invention provided on varying dental implants along with varying abutments.

FIG. 8 shows an arrangement similar to that of FIG. 5A wherein one or more slits 23 extending in a substantially parallel manner to the axis 7 of the implant 1 are provided in the cylindrical sleeve 15. By means of the slits 23 the cylindrical sleeve 15, which may be advantageously manufactured of a material showing resilient properties, may be compressed. In this way a better positioning of the abutment 6 on the implant 1 may be achieved.

The foregoing description of the invention, including a preferred embodiment thereof, has been presented for the purpose of illustration and description. It is not intended to be exhaustive nor is it intended to limit the invention to the precise form disclosed. It will be apparent to those skilled in the art that the disclosed embodiments may be modified in light of the above teachings. In particular, a person skilled in the art will readily understand that the shape or outline of the interface between the soft tissue apposition surface and the bone tissue apposition surface may be variated.

The embodiments described are chosen to provide an illustration of principles of the invention and its practical application to enable thereby one of ordinary skill in the art to utilize the invention in various embodiments and with various modifications as are suited to the particular use contemplated. Therefore, the foregoing description is to be considered exemplary, rather than limiting, and the true scope of the invention is that described in the following claims.

Where technical features mentioned in any claim are followed by reference signs, those reference signs have been included just for the sole purpose of increasing intelligibility of the claims and accordingly, such reference signs do not have any limiting effect on the scope of each element identified by way of example by such reference signs.

The invention claimed is:

1. An intraosteal dental implant including a bore in the form a blind hole, the bore being shaped and devised such as to rotationally secure an abutment receivable in the dental implant, the dental implant having an outer profile substantially radially symmetrical to a central axis,
    wherein the bore is provided with a substantially cylindrical sleeve extending substantially coaxially to the dental implant, wherein the dental implant includes an inner neck surface for engaging a complementary surface of the abutment, and the sleeve extending beyond the inner neck surface to define an intersection curve between the inner neck surface of the dental implant and the sleeve, the intersection curve not lying in a plane perpendicular to the central axis of the dental implant.

2. The intraosteal dental implant of claim 1, wherein the bore is adapted to rotationally secure an abutment comprising a downwardly extending protrusion with a lower surface exactly matching the inner neck surface of the dental implant.

3. The intraosteal dental implant of claim 2, wherein the bore is adapted to rotationally secure the abutment such that, in the assembled state of the abutment, the downwardly extending protrusion surrounds the sleeve and the lower surface rests on the inner neck surface.

4. The intraosteal dental implant of claim 3, further including a screw which fits into the sleeve with no or very little play.

5. The intraosteal dental implant of claim 1 further having a bone tissue apposition surface extending from a tip of the dental implant up to an interface at a neck portion of the dental implant, and a soft tissue apposition surface extending from the interface to a shoulder of the dental implant, wherein the shoulder is inclined with respect to the central axis of the dental implant.

6. The intraosteal dental implant of claim 5, wherein the shoulder is substantially contained in a plane.

7. The intraosteal dental implant of claim 5, wherein the shoulder has an inclination in the range from about 60° to about 80°.

8. The intraosteal dental implant of claim 5, wherein the shoulder has an inclination in the range from about 65° to about 75°.

9. The intraosteal dental implant of claim 5, wherein the shoulder has an inclination of about 70°.

10. The intraosteal dental implant of claims 5 wherein the neck portion of the dental implant has a palatal or lingual side and a labial side, and wherein the palatal or lingual side has a larger extension than the labial side.

11. The intraosteal dental implant of claim 5, wherein the interface is substantially parallel to the shoulder.

12. The intraosteal dental implant of claim 5, wherein the interface has a curved profile which is increasing from the labial side towards the interdental side and decreasing towards the palatal/lingual side.

13. The intraosteal dental implant of claim 5, wherein the interface is substantially perpendicular to the central axis.

14. The intraosteal dental implant of claim 5, wherein the interface has a curved profile which is increasing from the labial side towards the interdental side and a horizontal profile, substantially perpendicular to the axis from the interdental side towards the palatal/lingual side.

15. The intraosteal dental implant of claim 1, wherein the cylindrical sleeve is provided with one or more slits such as to allow compression of the cylindrical sleeve.

16. The intraosteal dental implant of claim 1, wherein the cylindrical sleeve is provided with one or more slits such as to allow compression of the cylindrical sleeve.

17. An intraosteal dental implant including a bore in the form a blind hole, the bore being shaped and devised such as to rotationally secure an abutment receivable in the dental implant, the dental implant having an outer profile substantially radially symmetrical to a central axis,
wherein the bore is provided with a substantially cylindrical sleeve extending coaxially to the dental implant, and wherein the dental implant includes an inner neck surface from which the sleeve extends upwardly, the inner neck surface of the dental implant having a substantially conical shape with an imaginary tip offset from the central axis of the dental implant.

18. The intraosteal dental implant of claim 17 wherein the bore is adapted to rotationally secure an abutment comprising a downwardly extending protrusion with a lower surface exactly matching the inner neck surface of the dental implant.

19. The intraosteal dental implant of claim 18, wherein the bore is adapted to rotationally secure the abutment such that, in the assembled state of the abutment, the downwardly extending protrusion surrounds the sleeve and the lower surface rests on the inner neck surface.

20. The intraosteal dental implant of claim 19, further including a screw which fits into the sleeve with no or very little play.

21. The intraosteal dental implant of claim 17 further having a bone tissue apposition surface extending from a tip of the dental implant up to an interface at a neck portion of the dental implant, and a soft tissue apposition surface extending from the interface to a shoulder of the dental implant, wherein the shoulder is inclined with respect to the central axis of the dental implant.

22. The intraosteal dental implant of claim 21, wherein the shoulder is substantially contained in a plane.

23. The intraosteal dental implant of claim 21, wherein the shoulder has an inclination in the range from about 60° to about 80°.

24. The intraosteal dental implant of claim 21, wherein the shoulder has an inclination in the range from about 65° to about 75°.

25. The intraosteal dental implant of claim 21, wherein the shoulder has an inclination of about 70°.

26. The intraosteal dental implant of claim 21, wherein the neck portion of the dental implant has a palatal or lingual side and a labial side, and wherein the palatal or lingual side has a larger extension than the labial side.

27. The intraosteal dental implant of claim 21, wherein the interface is substantially parallel to the shoulder.

28. The intraosteal dental implant of claim 21, wherein the interface has a curved profile which is increasing from the labial side towards the interdental side and decreasing towards the palatal/lingual side.

29. The intraosteal dental implant of claim 21, wherein the interface is substantially perpendicular to the central axis.

30. The intraosteal dental implant of claim 21, wherein the interface has a curved profile which is increasing from the labial side towards the interdental side and a horizontal profile, substantially perpendicular to the axis from the interdental side towards the palatal/lingual side.

\* \* \* \* \*